United States Patent
Kageyama (10) Patent No.: US 9,248,925 B2
(45) Date of Patent: Feb. 2, 2016

(54) MEDICINE SUPPLY APPARATUS (75) Inventor: Yu Kageyama, Hirakata (JP)

(73) Assignee: TAKAZONO TECHNOLOGY INCORPORATED, Hirakata-Shi, Osaka (JP)

( * ) Notice: Subject to any disclaimer, the term of this patent is extended or adjusted under 35 U.S.C. 154(b) by 239 days.

(21) Appl. No.: 13/821,219

(22) PCT Filed: Sep. 30, 2011

(86) PCT No.: PCT/JP2011/072555
§ 371 (c)(1),
(2), (4) Date: Mar. 6, 2013

(87) PCT Pub. No.: WO2012/046650
PCT Pub. Date: Apr. 12, 2012

(65) Prior Publication Data
US 2013/0180624 A1 Jul. 18, 2013

(30) Foreign Application Priority Data
Oct. 6, 2010 (JP) ................................. 2010-226359

(51) Int. Cl.
*B65B 1/04* (2006.01)
*B65B 5/10* (2006.01)
(Continued)

(52) U.S. Cl.
CPC . *B65B 1/04* (2013.01); *B65B 5/103* (2013.01); *G07F 5/26* (2013.01); *G07F 11/62* (2013.01); *G07F 17/0092* (2013.01); *G06F 19/3462* (2013.01)

(58) Field of Classification Search
CPC ....... B65B 1/04; B65B 5/103; G06F 19/3456; G06F 19/2462; G06F 19/3468; G07F 5/26; G07F 17/0092; E05B 65/462; A61B 19/0264; A61B 2019/0254; A61B 2019/0265; A61B 2019/0272
USPC ......... 312/209, 215–222, 283, 286, 290, 295, 312/310–311, 249.11, 326; 141/266; 700/231
See application file for complete search history.

(56) References Cited

U.S. PATENT DOCUMENTS 4,775,199 A * 10/1988 Lanius et al. ................. 312/220
5,176,281 A * 1/1993 Fiore ............................ 220/520
(Continued)

FOREIGN PATENT DOCUMENTS

CN 2112973 U 8/1992
CN 1511760 A 7/2004
(Continued)

OTHER PUBLICATIONS

International Preliminary Report on Patentability issued May 8, 2013 in corresponding International application No. PCT/JP2011/072555.
(Continued)

*Primary Examiner* — Daniel J Troy
*Assistant Examiner* — Ryan A Doyle
(74) *Attorney, Agent, or Firm* — Knobbe Martens Olson & Bear LLP (57) ABSTRACT

A medicine supply apparatus that subdivides and supplies medicines is provided. The medicine supply apparatus includes: a cassette unit that is provided movably between a fixed position and a drawn position, and can temporarily retain the medicines in a subdivided manner; a cover provided movably between a closed position to cover the cassette unit from above and an opened position where the cassette unit is exposed; and an association mechanism that associates operations of the cassette unit and the cover, wherein the association mechanism restricts an operation of the cover so as to keep the cover in the closed position when the cassette unit is in the drawn position.

5 Claims, 9 Drawing Sheets

(51) Int. Cl.
*G07F 5/26* (2006.01)
*G07F 11/62* (2006.01)
*G07F 17/00* (2006.01)
G06F 19/00 (2011.01)

(56) References Cited

U.S. PATENT DOCUMENTS

| | | | | |
|---|---|---|---|---|
| 6,719,380 | B1* | 4/2004 | Liu | 312/218 |
| 2004/0129595 | A1* | 7/2004 | Dane et al. | 206/503 |
| 2004/0169447 | A1* | 9/2004 | Bezzubov | 312/111 |
| 2006/0181182 | A1* | 8/2006 | Hung | 312/218 |
| 2007/0273255 | A1* | 11/2007 | Purdy | 312/221 |
| 2008/0314002 | A1 | 12/2008 | Yuyama et al. | |
| 2010/0224527 | A1* | 9/2010 | Huang | 206/503 |

FOREIGN PATENT DOCUMENTS

| | | |
|---|---|---|
| CN | 2782865 Y | 5/2006 |
| CN | 101541294 A | 9/2009 |
| CN | 201516959 U | 6/2010 |
| JP | 11-197216 A | 7/1999 |
| JP | 2006-232351 A | 7/2006 |
| JP | 2006-238986 A | 9/2009 |
| JP | 2010-018335 A | 1/2010 |
| KR | 10-2006-0094679 A | 8/2006 |
| KR | 10-2009-0088612 A | 8/2009 |
| WO | 99/30248 A1 | 6/1999 |

OTHER PUBLICATIONS

Extended European Search Report issued Mar. 18, 2014 in corresponding European Application No. 11830582.0.

* cited by examiner

MEDICINE SUPPLY APPARATUS

CROSS-REFERENCE TO RELATED APPLICATION

This application is the U.S. National Phase under 35. U.S.C. §371 of International Application PCT/JP2011/072555, filed Sep. 30, 2011, which claims priority to Japanese Patent Application No. 2010-226359, filed Oct. 6, 2010. The disclosures of the above-described applications are hereby incorporated by reference in their entirety. The International Application was published under PCT Article 21(2) in a language other than English.

TECHNICAL FIELD

The present invention relates to a medicine supply apparatus that can subdivide and supply medicines.

BACKGROUND ART

A medicine dispensing and packing apparatus or the like includes a medicine supply apparatus that can subdivide and supply medicines such as pills. For example, a medicine supply apparatus provided in a "medicine packing apparatus" is described in Patent Document 1.

The medicine supply apparatus is referred to as a "pill supply unit" in Patent Document 1. The pill supply unit is provided on an upper surface of the medicine packing apparatus, and includes a pill housing portion having a plurality of pill housing boxes in a matrix. An operator such as a pharmacist manually dispenses and supplies pills into the pill housing portion. At this time, a pill for one package is supplied into each of the pill housing boxes.

A pill ejection portion is provided below the pill housing box (inside the apparatus). The pill ejection portion can automatically take out (eject) the pill supplied into the pill housing box as described above and supply the pill into a packing unit in the apparatus.

In the medicine packing apparatus described in Patent Document 1, the pill supply unit is secured to a body of the apparatus. As described above, the pill supply unit is provided on the upper surface of the medicine packing apparatus. Thus, if the operator is short, he/she has to considerably extend his/her arm to supply pills into the pill housing boxes close to a back side, which may cause difficulty in operation. This is particularly noticeable for a large medicine packing apparatus in which many pill housing boxes are arranged in a depth direction.

Thus, the present inventor has found a structure in which a part of a medicine supply apparatus can be drawn toward a front side (a side on which an operator stands). More specifically, this structure is such that a top tablet cassette unit (hereinafter referred to as a "cassette unit") corresponding to the "pill housing portion" in Patent Document 1 can be drawn from a body of a medicine packing apparatus. This reduces a distance between the operator and the cassette unit, and facilitates an operation even for a short operator.

CITATION LIST

Patent Document

Patent Document 1: Japanese Patent Laid-Open No. 2010-18335

SUMMARY OF INVENTION

Technical Problem

However, in such a structure in which the cassette unit can be drawn, a space is created in a part where the cassette unit is originally located when the cassette unit is drawn out. Thus, the operator may place a medicine into this space by mistake, or foreign matter such as a medicine of a different type may be mixed in the medicine packing apparatus, which may cause trouble such as a preparation error.

Therefore, it is an object of the present invention to provide a medicine supply apparatus that can prevent foreign matter from being mixed in the apparatus when a cassette unit is drawn out.

SOLUTION TO PROBLEM

The present invention provides a medicine supply apparatus that subdivides and supplies medicines, including: a cassette unit that is provided movably between a fixed position where the medicines can be supplied and a drawn position displaced from the fixed position, and can temporarily retain the medicines in a subdivided manner; a cover provided movably between a closed position to cover the cassette unit from above and an opened position where the cassette unit is exposed when the cassette unit is held at the fixed position; and an association mechanism that associates operations of the cassette unit and the cover, wherein the association mechanism restricts the operation of the cover so as to keep the cover at the closed position when the cassette unit is held at the drawn position.

According to the above configuration, the association mechanism restricts the operation of the cover so as to keep the cover at the closed position. Thus, when the cassette unit is held at the drawn position, the cover can cover the space created in a part from which the cassette unit is drawn.

The present invention also provides a medicine supply apparatus that subdivides and supplies medicines, including: a cassette unit that is provided movably between a fixed position where the medicines can be supplied and a drawn position displaced from the fixed position, and can temporarily retain the medicines in a subdivided manner; a cover provided movably between a closed position to cover the cassette unit from above and an opened position where the cassette unit is exposed when the cassette unit is held at the fixed position; and an association mechanism that associates operations of the cassette unit and the cover, wherein the association mechanism restricts the operation of the cassette unit so as to keep the cassette unit at the fixed position when the cover is held at the opened position.

According to the above configuration, the association mechanism restricts the operation of the cassette unit so as to keep the cassette unit at the fixed position. This prevents the cassette unit from being drawn to create a space when the cover is held at the opened position.

The present invention provides a medicine supply apparatus that subdivides and supplies medicines, including: a cassette unit that is provided movably between a fixed position where the medicines can be supplied and a drawn position displaced from the fixed position, and can temporarily retain the medicines in a subdivided manner; a cover provided movably between a closed position to cover the cassette unit from above and an opened position where the cassette unit is exposed when the cassette unit is held at the fixed position; and an association mechanism that associates operations of the cassette unit and the cover, wherein the association mechanism includes a cover restriction portion that restricts the operation of the cover so as to keep the cover at the closed position when the cassette unit is held at the drawn position, and a cassette unit restriction portion that restricts the operation of the cassette unit so as to keep the cassette unit at the fixed position when the cover is held at the opened position.

According to the above configuration, the cover restriction portion restricts the operation of the cover so as to keep the cover at the closed position. Thus, when the cassette unit is held at the drawn position, the cover can cover the space created in a part from which the cassette unit is drawn. The cassette unit restriction portion restricts the operation of the cassette unit so as to keep the cassette unit at the fixed position. This can prevent the cassette unit from being drawn to create a space when the cover is held at the opened position.

In this case, an aspect as described below may be allowed. The cover restriction portion includes a first cover restriction member provided on either the cover or the cassette unit, and a second cover restriction member provided on the other, the first cover restriction member has a hooking portion, the second cover restriction member has a hooked portion to be able to be hooked by the hooking portion, and an open portion where the hooked portion is not provided, the cover restriction portion is configured so that when the cassette unit is at least at the drawn position, the hooking portion is hooked on the hooked portion to restrict movement of the cover to the opened position, and the cover restriction portion is configured so that when the cassette unit is held at the fixed position, the hooking portion passes through the open portion to allow the cover to be moved to the opened position.

According to this configuration, the hooking portion, the hooked portion, and the open portion can constitute the cover restriction portion. Thus, even with a relatively simple configuration, the operation of the cover can be restricted and allowed so as to keep the cover at the closed position.

Another aspect as described below may be allowed. The cassette unit restriction portion includes a first cassette unit restriction member provided on a portion other than the cassette unit, and a second cassette unit restriction member provided on the cassette unit, and the first cassette unit restriction member operates in association with opening and closing of the cover, and engages the second cassette unit restriction member so as to restrict drawing of the cassette unit when the cover is held at the opened position.

According to this configuration, the first cassette unit restriction member, and the second cassette unit restriction member that engages the first cassette unit restriction member together can constitute the cassette unit restriction portion. Thus, even with a relatively simple configuration, the operation of the cassette unit can be restricted so as to keep the cassette unit at the fixed position.

Advantageous Effect of Invention

According to the present invention, the cover can cover the space created in a part from which the cassette unit is drawn. This can prevent foreign matter from being mixed in the apparatus when the cassette unit is drawn.

DESCRIPTION OF EMBODIMENT

Now, an embodiment of the present invention will be described. For wordings of directions in the below description, "upper or lower" refers to a positional relationship in a state shown in FIG. 1, "front" refers to a front side and "back" refers to a back side in the state shown in FIG. 1. The wordings of the directions are used for convenience of description, and not used for construing the invention in a limited manner.

Figure 1:
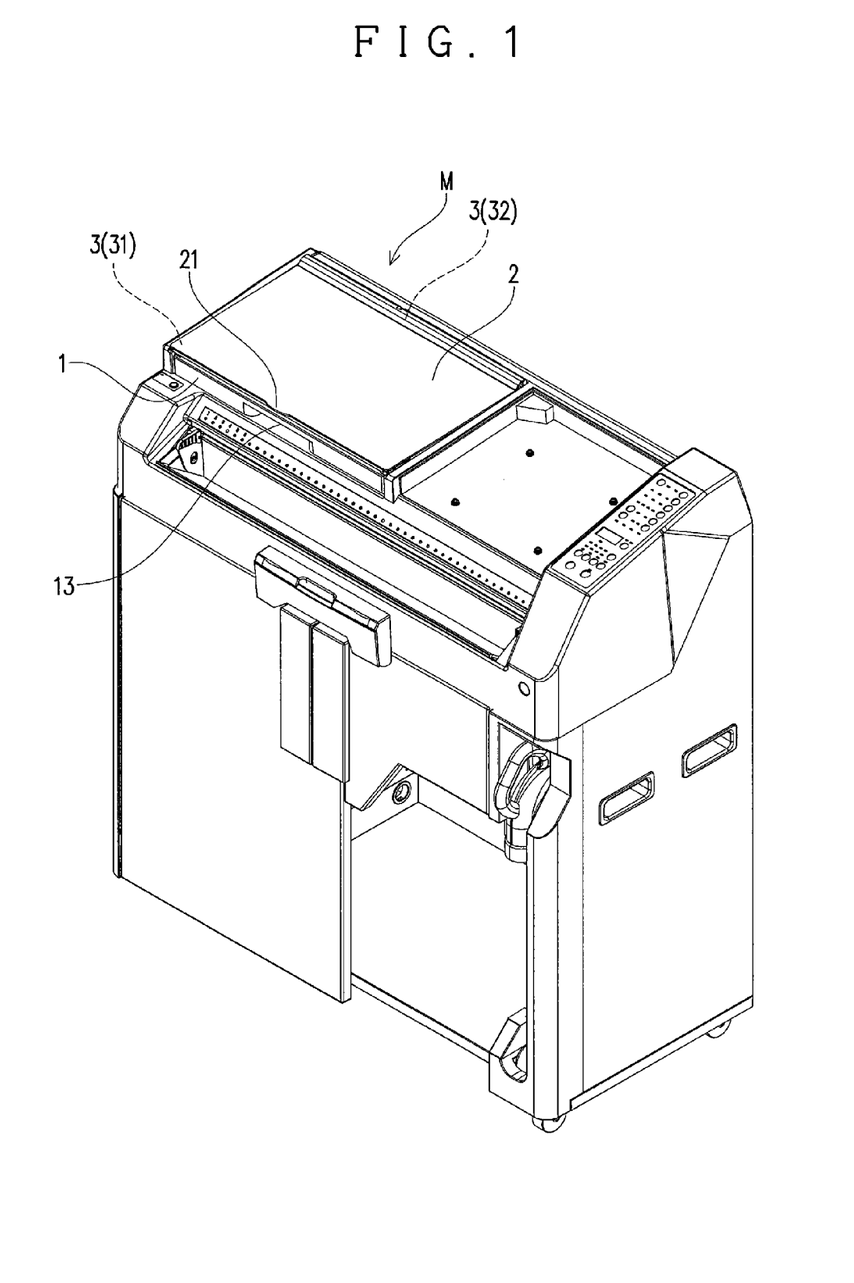
FIG. 1 is a perspective view, seen from front, of a medicine dispensing and packing apparatus including a medicine supply apparatus of this embodiment, with an inner mechanism being omitted.

A medicine supply apparatus M of this embodiment can subdivide and supply medicines. For example, as shown in FIG. 1, the medicine supply apparatus M is incorporated into a medicine dispensing and packing apparatus. The medicines to be subdivided include medicines other than gaseous, liquid, powder, or granular medicines (except encapsulated ones) and that can be manually picked up and divided by an operator such as a pharmacist in a predetermined dose (a dose for one package). For example, the medicines include pills or capsules.

Figure 2:
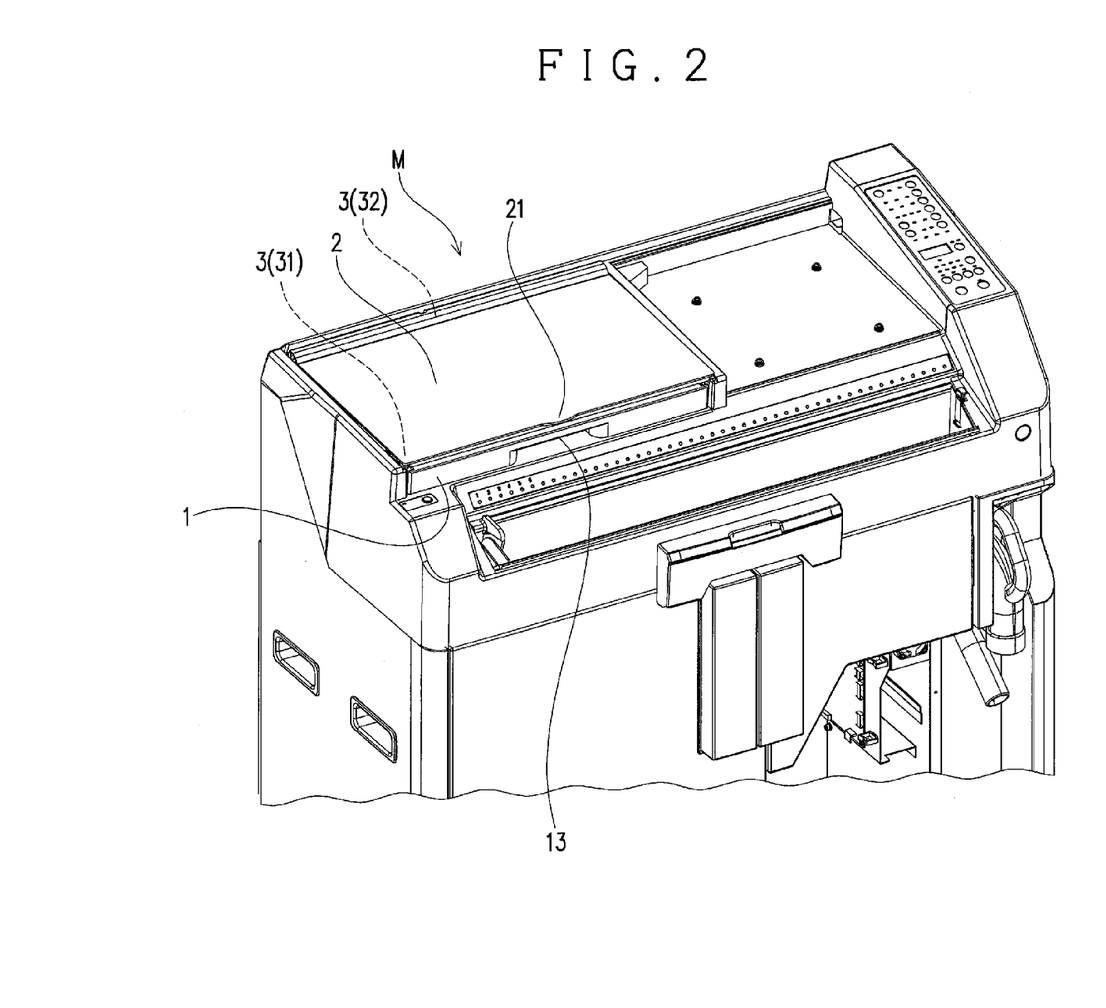
FIG. 2 is a perspective view showing an upper portion of the medicine dispensing and packing apparatus, with a cassette unit held at a fixed position and a cover held at a closed position.
Figure 3:
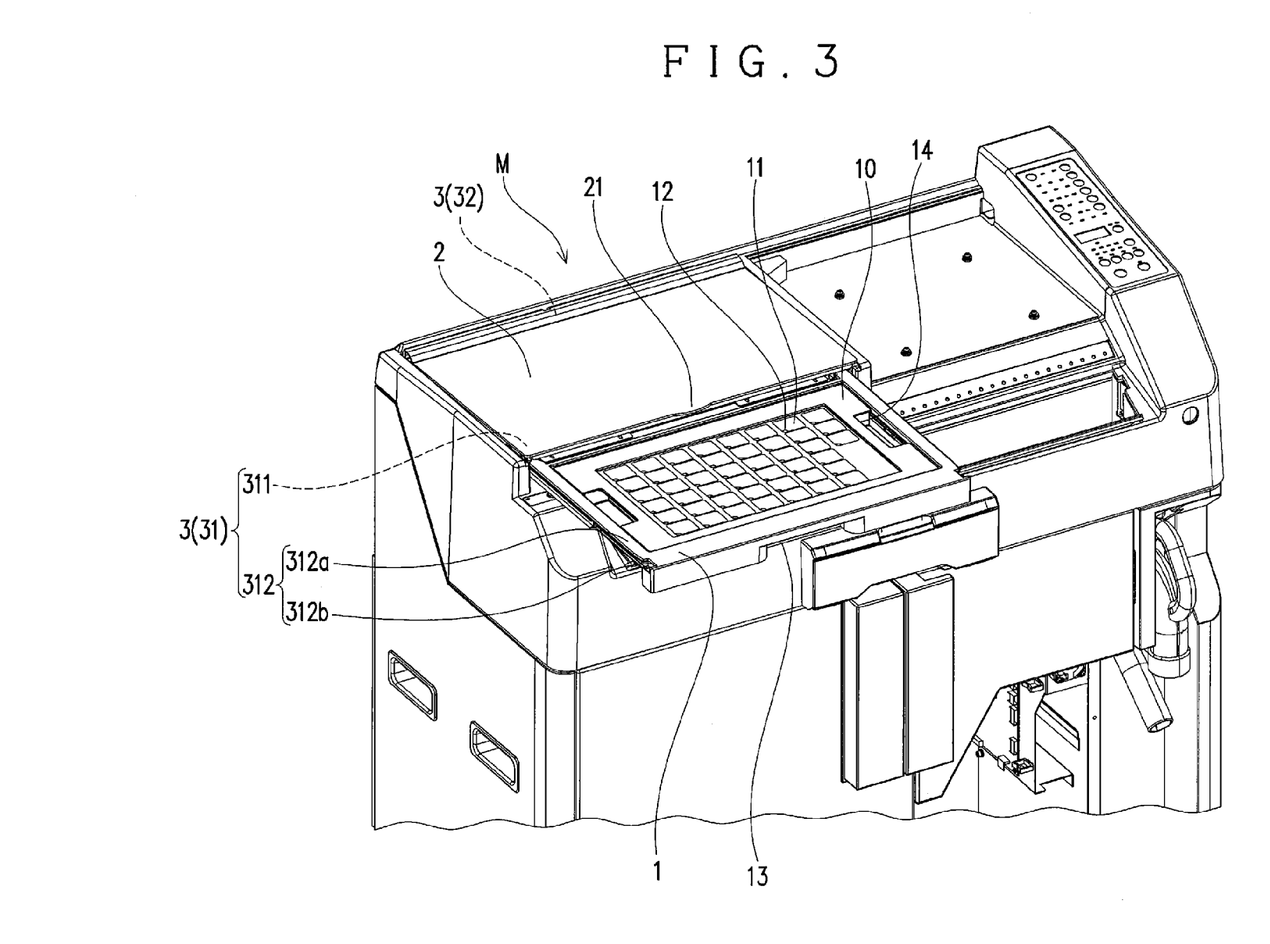
FIG. 3 is a perspective view showing the upper portion of the medicine dispensing and packing apparatus, with the cassette unit held at a drawn position and a cover held at the closed position.

The medicine supply apparatus M includes a cassette unit 1, a cover 2, and an association mechanism 3. The cassette unit 1 is provided movably between a fixed position (see FIGS. 2 and 4) where the medicines can be supplied to a next step, and a drawn position (see FIG. 3) displaced from the fixed position. As shown in FIG. 3, in an upper portion of the cassette unit 1, a plurality of medicine subdivision boxes 11 are provided in parallel in a depth direction and a lateral direction in the drawing. Upper and lower sides of the medicine subdivision boxes 11 are open. An opening/closing shutter 12 is provided in a lower portion of the cassette unit 1 (see FIG. 9) so that a lower end of the medicine subdivision boxes 11 can be opened and closed. Thus, when the opening/closing shutter 12 is closed, the medicines can be temporarily retained in a subdivided manner in the medicine subdivision boxes 11. When the opening/closing shutter 12 is opened, the medicines can drop downward from the medicine subdivision boxes 11, and can be supplied to an under-tablet cassette (not shown) provided below the cassette unit 1. Like a conventional medicine supply apparatus, a shutter is also provided in a lower portion of the under-tablet cassette. Thus, the medicines for each package can be supplied to a dispensing and packing apparatus provided further below the under-tablet cassette (not shown) by opening the shutter. The cassette unit 1 is drawn out by an operator. For this purpose, in order for the operator to easily place his/her hand, a cutout is formed in a front side of the cassette unit 1 to provide a pull 13.

Figure 4:
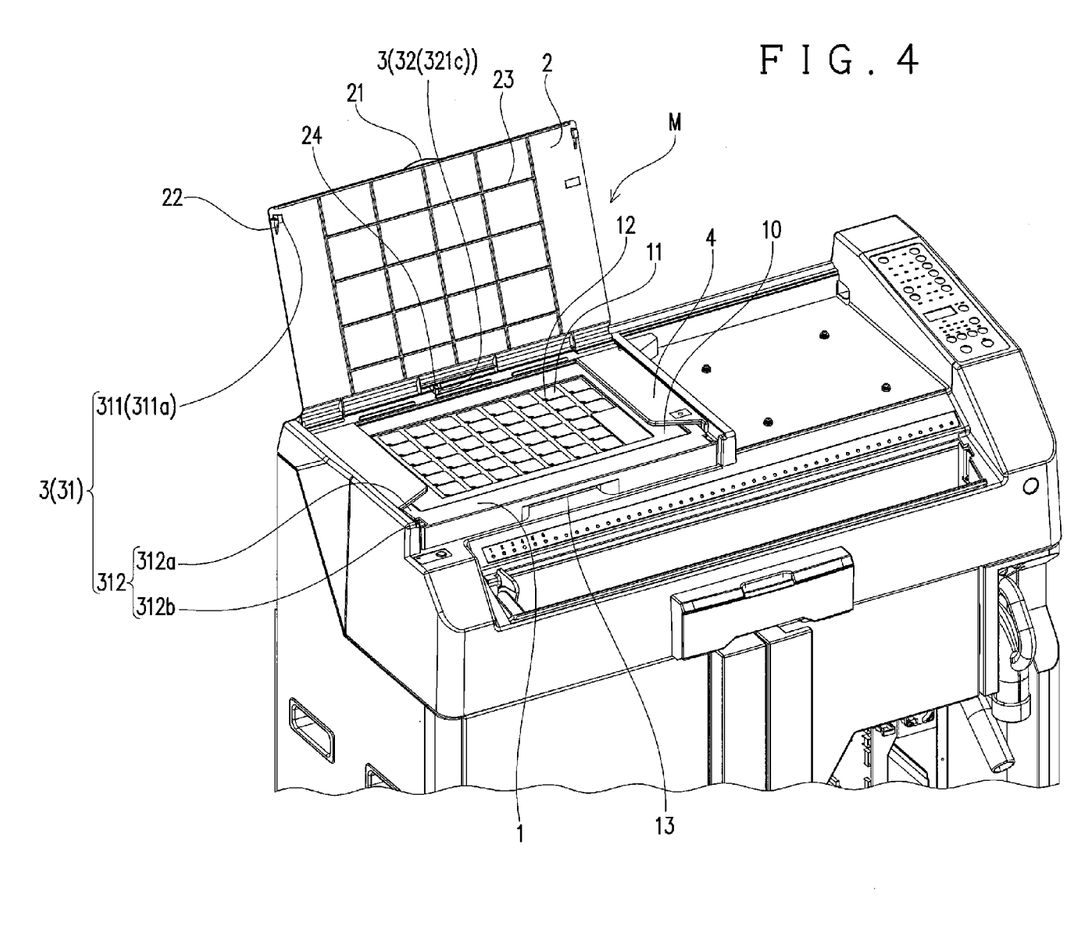
FIG. 4 is a perspective view showing the upper portion of the medicine dispensing and packing apparatus, with the cassette unit held at the fixed position and the cover held at an opened position.

The cover 2 is provided movably between a closed position (see FIGS. 2 and 3) to cover the cassette unit 1 from above, and an opened position (see FIG. 4) where the cassette unit 1 is exposed. The cover 2 in this embodiment is in a form of a sheet of plate. A hinge is provided at an end of a back side of the cover 2 (far side in the Figure) so that the cover 2 is pivotable between the closed position and the opened position. A handle 21 is provided to protrude from a front end of the cover 2. Thus, the operator can hold the handle 21 to pivot the cover 2. In this embodiment, the handle 21 protrudes toward a front side. As shown in FIG. 4, two pawls 22 protrude from an inner surface of the cover 2 closer to the front. A tip of each pawl 22 is bent to face. The bent portion forms a hooking portion 311a of the association mechanism 3 described later. When the cover 2 is held at the opened position, the operator such as the pharmacist can manually dispense and supply the medicines into the medicine subdivision boxes 11 in the cassette unit 1.

The cover 2 is not limited to that in this embodiment, but may be implemented in various aspects, for example, a cover that horizontally slides, a cover that generally moves upward, or a cover having a hinge for folding the cover in a middle into an opened position. A reinforcement portion such as a rib 23 shown in FIG. 4 may be provided on a front surface or a back surface of the cover 2 so as to prevent the cover 2 from being bent even when an object is placed on the cover 2. As shown in FIG. 4 or the like, the cover 2 in this embodiment is formed of a sheet of plate, but besides, the cover 2 may be formed of a plurality of overlapping plates (specifically, two outer and inner cover pieces, or three or more cover pieces). When the cover is thus formed of a plurality of cover pieces, a prescription may be held between the plurality of cover pieces to hold the prescription in a position easily seen by the operator with the cover pieces being raised.

The operator often stands and operates on the front side of the medicine dispensing and packing apparatus. As described above, the cassette unit 1 is provided movably between the fixed position and the drawn position. Thus, when the cassette unit 1 is moved to the drawn position, a distance between the operator and the cassette unit 1 is reduced. Thus, even a short operator can comfortably place his/her hand on all the medicine subdivision boxes 11, thereby facilitating manual distribution of the medicines. When the cassette unit 1 is thus held at the drawn position, a cassette body 10 as a part of the cassette unit 1 can be removed to facilitate cleaning or the like. As shown in FIG. 3, the cassette body 10 can be easily removed by holding handles 14 provided on left and right sides of the cassette body 10 in the Figure.

The association mechanism 3 associates the operations of the cassette unit 1 and the cover 2. The association mechanism 3 includes a cover restriction portion 31 and a cassette unit restriction portion 32. The cover restriction portion 31 restricts the operation of the cover 2 so as to keep the cover 2 at the closed position when the cassette unit 1 is held at the drawn position. The cassette unit restriction portion 32 restricts the operation of the cassette unit 1 so as to keep the cassette unit 1 at the fixed position when the cover 2 is held at the opened position. Thus, the cover 2 is held at the opened position when the cassette unit 1 is held at the drawn position, thereby preventing a situation where a space is created in a part where the cassette unit is originally located, an under-tablet cassette is exposed, and foreign matter or the like is mixed in the medicine supply apparatus M.

When the cover 2 is formed of a plurality of overlapping plates as described above, the association mechanism 3 may restrict an operation of only the inner cover piece, and other parts such as the outer cover piece may be freely opened and closed irrespective of the position of the cassette unit 1.

The cover restriction portion 31 includes a first cover restriction member 311 and a second cover restriction member 312. In this embodiment, the first cover restriction member 311 is provided on the cover 2, and the second cover restriction member 312 is provided on the cassette unit 1. On the contrary, the first cover restriction member 311 may be provided on the cassette unit 1, and the second cover restriction member 312 may be provided on the cover 2.

The first cover restriction member 311 has a hooking portion 311a. The hooking portion 311a is formed at a tip of the pawl 22 provided on the inner surface of the cover 2 as described above.

The second cover restriction member 312 includes a hooked portion 312a provided in parallel with a drawing direction of the cassette unit 1, and an open portion 312b where the hooked portion 312a is not provided.

Figure 5:
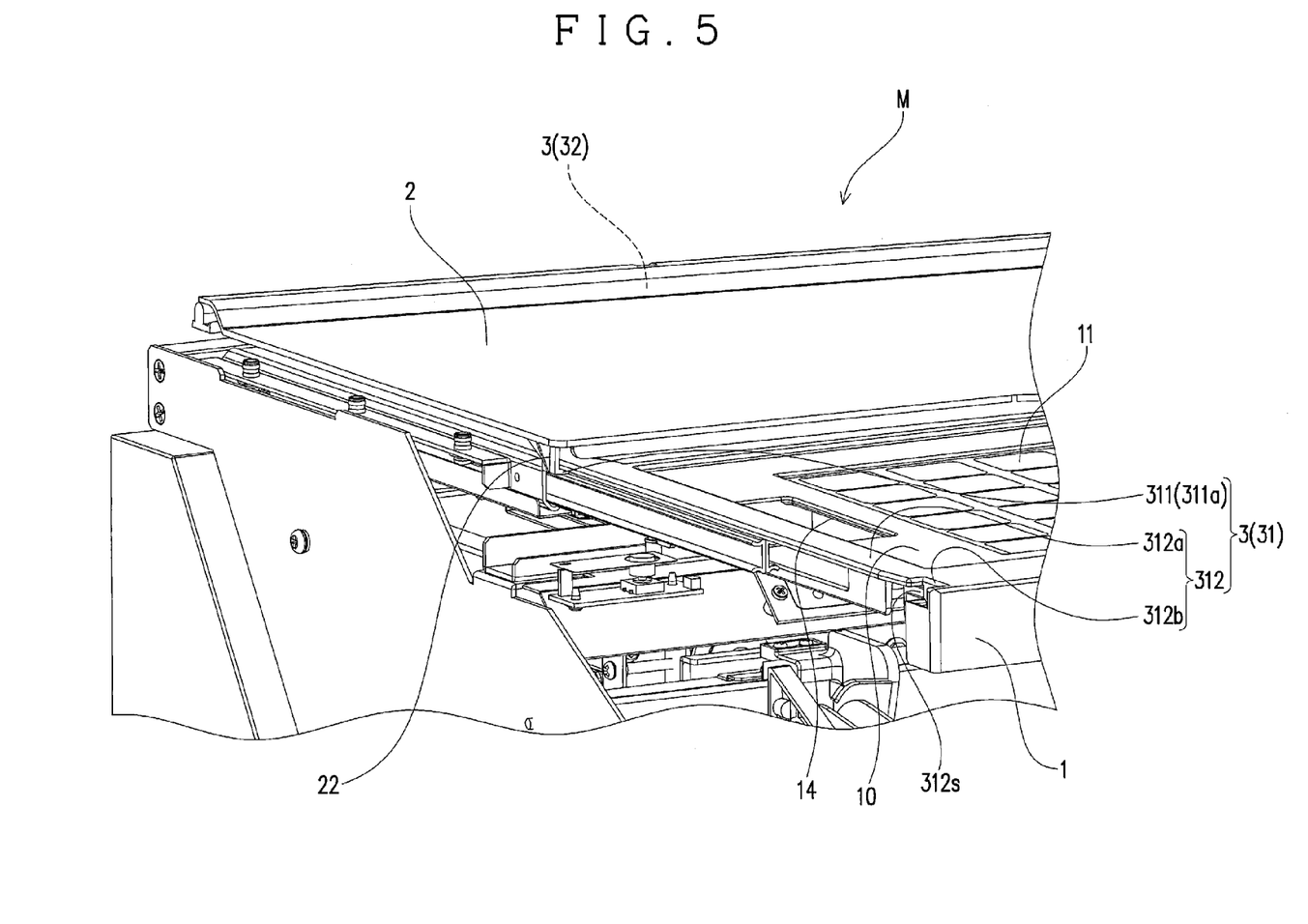
FIG. 5 is an enlarged perspective view of essential portions of the medicine supply apparatus of this embodiment, with the cassette unit held at the drawn position and the cover held at the closed position.

The hooked portion 312a is hooked by the hooking portion 311a to restrict movement of the cover 2 to the opened position. Specifically, the hooked portion 312a overhangs like a hood from a lateral end of the cassette unit 1 in the Figures (see FIGS. 5 to 7). Thus, when the cassette unit 1 is held at least at the drawn position (in other words, the cassette unit 1 is not held at the fixed position), the hooked portion 312a is hooked by the hooking portion 311a and thus restricts movement of the cover 2 to the opened position.

Figure 6:
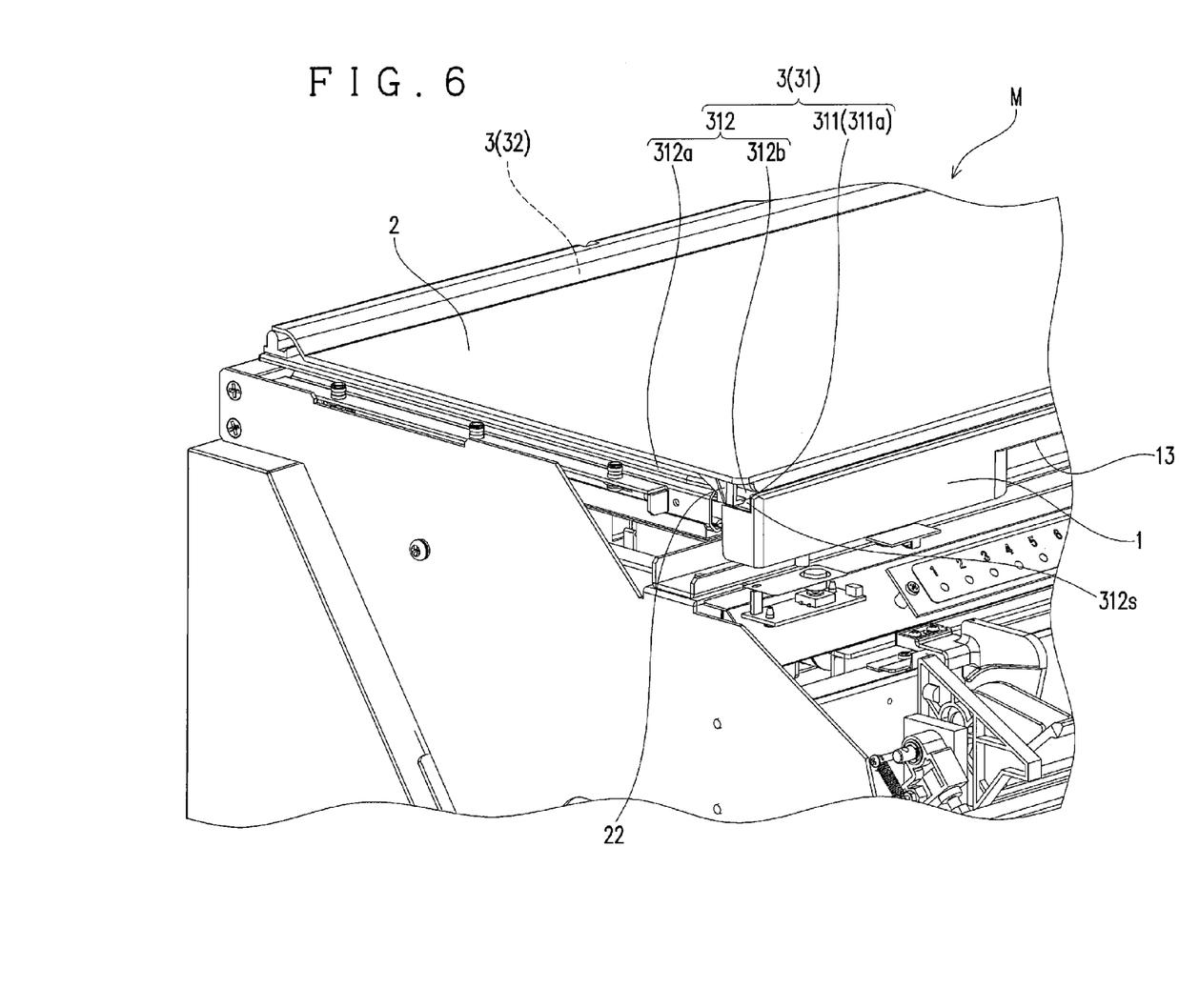
FIG. 6 is an enlarged perspective view of essential portions of the medicine supply apparatus of this embodiment, with the cassette unit held at the fixed position and the cover held at the closed position.
Figure 7:
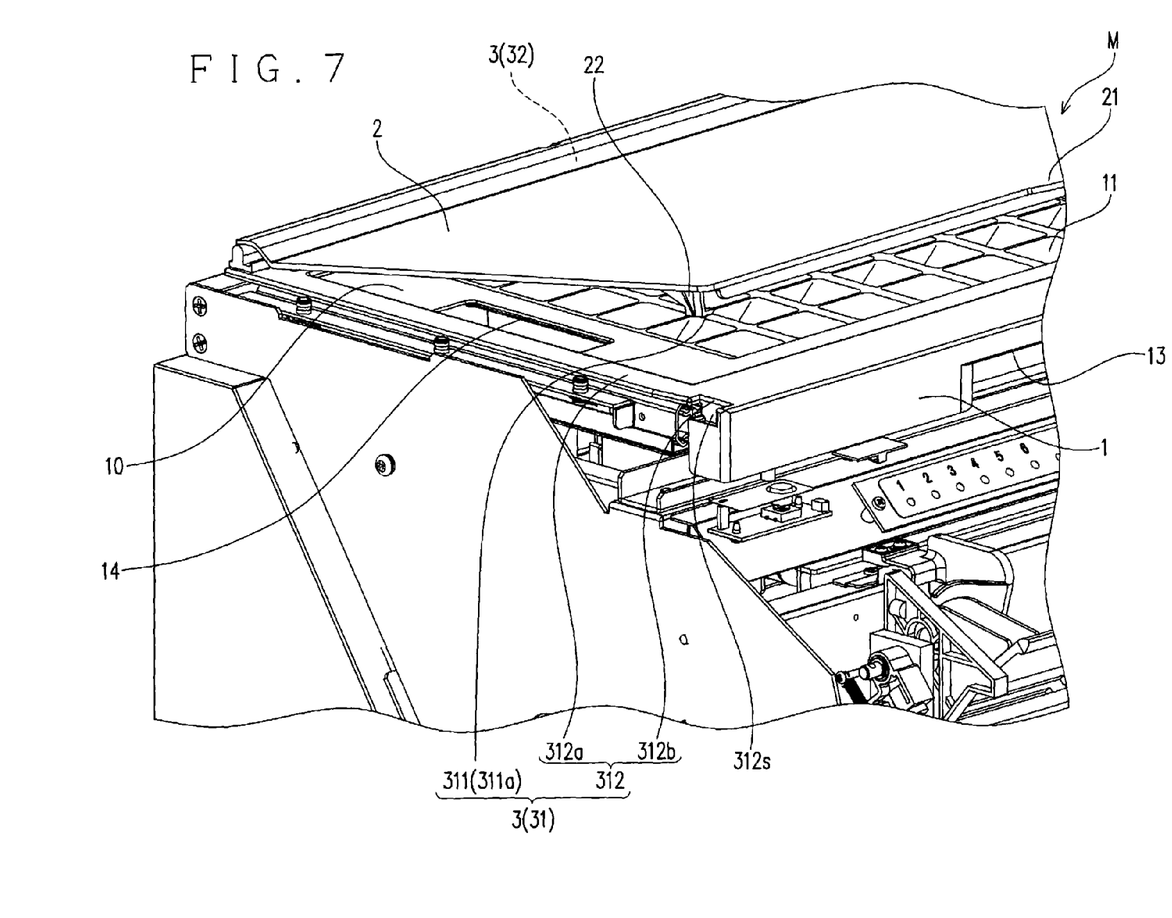
FIG. 7 is an enlarged perspective view of essential portions of the medicine supply apparatus of this embodiment, with the cassette unit held at the fixed position and the cover being moved to the opened position.

In the open portion 312b, a space 312s is formed that does not interfere with relative movement with respect to the hooking portion 311a when the cover 2 is moved to the opened position. Specifically, the space 312s is a portion where the hooked portion 312a ends in a portion close to the front in the lateral end of the cassette unit 1 in the Figures. The space 312s vertically extends in the open portion 312b. With movement of the cover 2 from the closed position to the opened position, the hooking portion 311a moving upward passes through the space 312s. Thus, as shown in FIG. 6, the hooking portion 311a matches the open portion 312b when the cover 2 is held at the closed position and the cassette unit 1 is held at the fixed position. Thus, when the cassette unit 1 is held at the fixed position, the hooking portion 311a passes through the space 312s in the open portion 312b, and thus the hooked portion 312a allows the cover 2 to be moved to the opened position.

Figure 8:
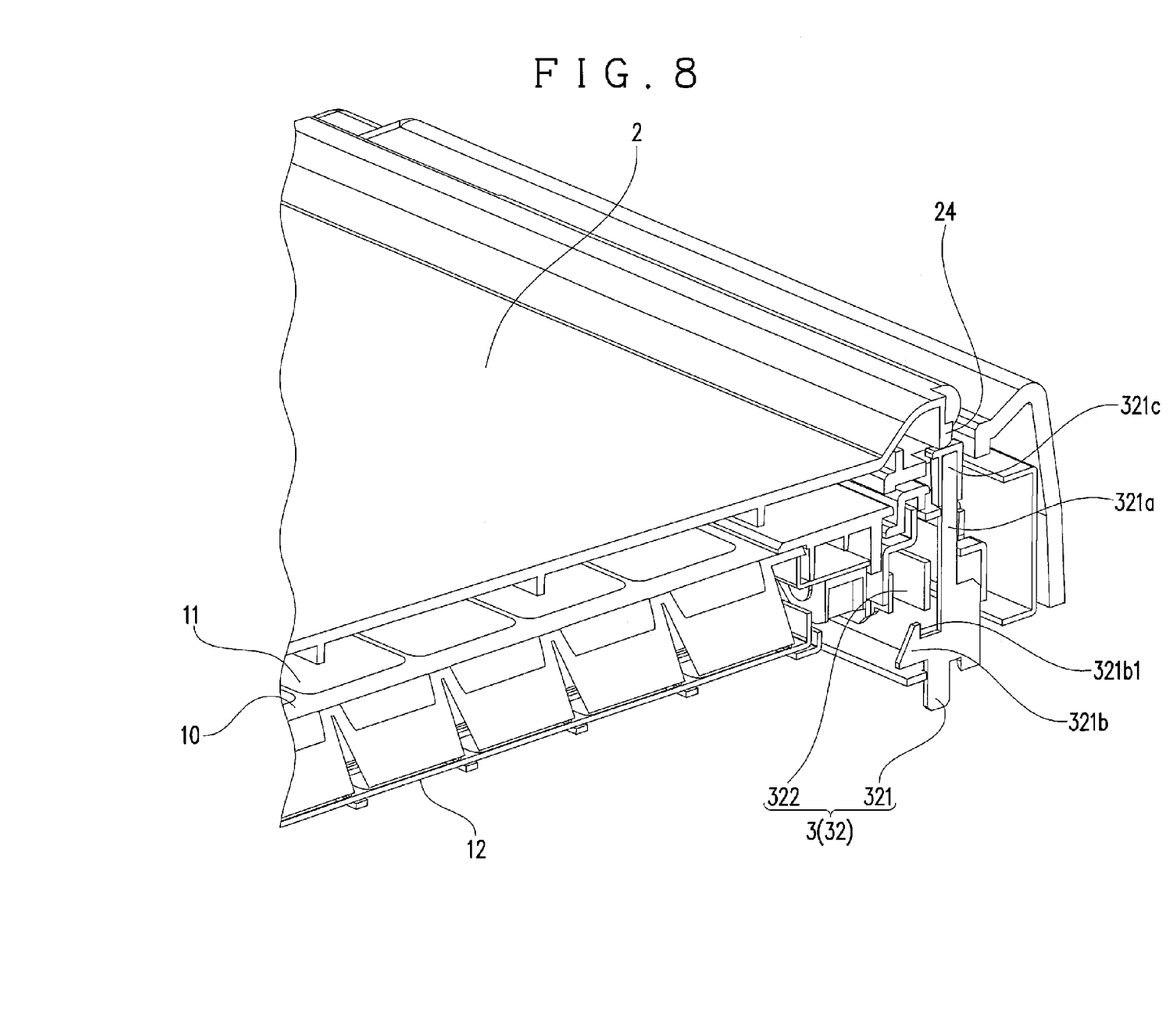
FIG. 8 is an enlarged perspective view of essential portions of the medicine supply apparatus of this embodiment, with a cassette unit restriction portion being out of operation.
Figure 9:
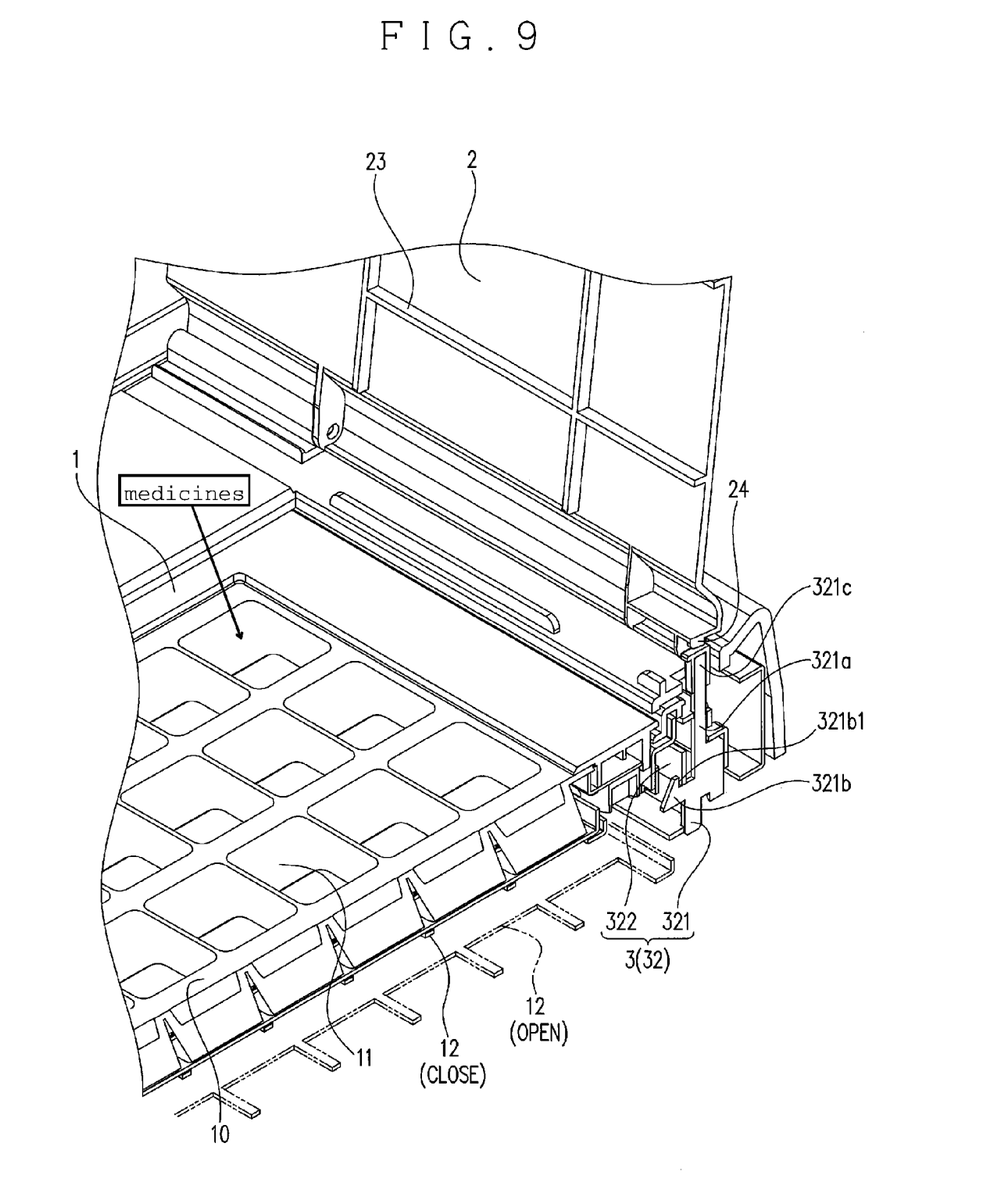
FIG. 9 is an enlarged perspective view of essential portions of the medicine supply apparatus of this embodiment, with the cassette unit restriction portion being in operation.

As shown in FIGS. 8 and 9, the cassette unit restriction portion 32 includes a first cassette unit restriction member 321 provided on a portion other than the cassette unit 1 in the medicine supply apparatus M, and a second cassette unit restriction member 322 provided on the cassette unit 1.

The first cassette unit restriction member 321 operates with opening and closing of the cover 2. The first cassette unit restriction member 321 in this embodiment includes a shaft 321a, a pawl 321b, and a pressed portion 321c. The shaft 321a is vertically formed, and an upper end of the shaft 321a is the pressed portion 321c. The pawl 321b is an upward pawl portion that protrudes from a lower portion of the shaft 321a toward the front. An engagement portion 321b1 is formed on a back side of the pawl 321b.

As shown in FIG. 9, the second cassette unit restriction member 322 engages the first cassette unit restriction member 321 so as to restrict drawing of the cassette unit 1 when the cover 2 is held at the opened position. The second cassette unit restriction member 322 in this embodiment is formed of a plate provided in parallel with a back surface of the cassette unit 1, and is hooked by the pawl 321b of the first cassette unit restriction member 321.

The shaft 321a of the first cassette unit restriction member 321 is constantly biased by a spring (not shown). Thus, as shown in FIG. 9, the pressed portion 321c protrudes upward. The pressed portion 321c is pressed by a pressing portion 24 that is a protrusion provided on the back surface of the cover 2 as shown in FIG. 8 to move the shaft 321a downward. With the shaft 321a being moved downward, the pawl 321b is not hooked on the second cassette unit restriction member 322, and thus the cassette unit 1 is movable in the drawing direction. Thus, as shown in FIG. 8, the cassette unit 1 can be drawn when the cover 2 is held at the closed position.

As shown in FIG. 9, when the cover 2 is held at the opened position, the shaft 321a of the first cassette unit restriction member 321 is biased by the spring and returned to an upper position. Thus, the engagement portion 321b1 of the pawl 321b abuts against the second cassette unit restriction member 322. The engagement portion 321b1 of the pawl 321b is located on the front side of the second cassette unit restriction member 322, thereby preventing the cassette unit 1 from being moved in the drawing direction. As such, the operation of the cassette unit 1 is restricted by the cassette unit restriction portion 32 so as to keep the cassette unit 1 at the fixed position.

As described above, the association mechanism 3 in this embodiment causes engagement between one and the other members to physically restrict the operation of the cassette unit 1 or the cover 2, but not limited to this. For example, the cassette unit 1 or the cover 2 may be motor-driven, and energization to a motor may be controlled to restrict the operation of the cassette unit 1 or the cover 2. The control of energization may be performed by, for example, detecting the position of the cassette unit 1 or the cover 2 using a sensor.

Even when the operation of the cassette unit 1 or the cover 2 is physically restricted, the cover restriction portion 31 and the cassette unit restriction portion 32 may be interlocked by a link mechanism or the like rather than independently provided as in the this embodiment.

The medicine supply apparatus M in this embodiment includes cassette unit removal restriction portions 4 that restrict movement of the cassette unit 1 in a removal direction different from the direction of the movement between the fixed position and the drawn position. In this embodiment, upward movement of the cassette body 10 as a part of the cassette unit 1 from the fixed position is restricted. The cassette unit removal restriction portions 4 are shown in FIG. 4, and overhang from lateral outer portions of the cassette unit 1 in the medicine supply apparatus M so as to face each other and cover an upper side of the cassette unit 1 (particularly, the cassette body 10).

When the cassette unit 1 is held at the fixed position, the cassette unit removal restriction portion 4 is located above the cassette unit 1 (particularly, the cassette body 10). Thus, in this embodiment, the cassette body 10 of the cassette unit 1 cannot be removed upward. This can prevent a situation where the cassette body 10 is unexpectedly removed, the under-tablet cassette is exposed, and foreign matter is mixed in the medicine supply apparatus M. When the cassette unit 1 is held at the drawn position, the cassette unit removal restriction portion 4 does not restrict upward movement of the cassette unit 1 (particularly, the cassette body 10). Thus, the cassette body 10 can be removed to easily clean dust or the like.

The cassette body 10 may be removed, and the operator may manually dispense the medicines in the medicine subdivision boxes 11 in the removed cassette body 10. Thus, the medicines can be easily supplied without limitation of space. When a plurality of cassette bodies 10 are prepared, the operator can change a cassette body 10 to which the medicines are completely supplied (manually dispensed) with an empty cassette body 10 from which pills are ejected, thereby allowing efficient supply of medicines in the medicine supply apparatus M, and subsequent efficient dispensing and packing in the medicine dispensing and packing apparatus.

REFERENCE SIGNS LIST 1 cassette unit
2 cover
3 association mechanism
31 cover restriction portion
311 first cover restriction member
311a hooking portion
312 second cover restriction member
312a hooked portion
312b open portion
312s space
32 cassette unit restriction portion
321 first cassette unit restriction member
322 second cassette unit restriction member
M medicine supply apparatus

What is claimed is:

1. A medicine supply apparatus that subdivides and supplies medicines, comprising:
   a cassette unit that is provided movably between a fixed position where the medicines can be supplied and a drawn position displaced from the fixed position, and can temporarily retain the medicines in a subdivided manner, the cassette unit including a lower end which is configured to be opened at the fixed position to thereby supply the retained medicines downward;
   a cover provided movably between a closed position to cover the cassette unit from above and an opened position where the cassette unit is exposed when the cassette unit is held at the fixed position; and
   an association mechanism that associates operations of the cassette unit and the cover,
   wherein a space is created at the fixed position of the cassette unit when the cassette unit is held at the drawn position, and
   wherein the association mechanism restricts the operation of the cover so as to keep the cover at the closed position, at which the cover covers the space, when the cassette unit is held at the drawn position.

2. A medicine supply apparatus that subdivides and supplies medicines, comprising:
   a cassette unit that is provided movably between a fixed position where the medicines can be supplied and a drawn position displaced from the fixed position, and can temporarily retain the medicines in a subdivided manner, the cassette unit including a lower end which is configured to be opened at the fixed position to thereby supply the retained medicines downward;
   a cover provided movably between a closed position to cover the cassette unit from above and an opened position where the cassette unit is exposed when the cassette unit is held at the fixed position; and an association mechanism that associates operations of the cassette unit and the cover, wherein a space is created at the fixed position of the cassette unit when the cassette unit is held at the drawn position, and wherein the association mechanism restricts the operation of the cassette unit so as to keep the cassette unit at the fixed position when the cover is held at the opened position.

3. A medicine supply apparatus that subdivides and supplies medicines, comprising:

a cassette unit that is provided movably between a fixed position where the medicines can be supplied and a drawn position displaced from the fixed position, and can temporarily retain the medicines in a subdivided manner, the cassette unit including a lower end which is configured to be opened at the fixed position to thereby supply the retained medicines downward;

a cover provided movably between a closed position to cover the cassette unit from above and an opened position where the cassette unit is exposed when the cassette unit is held at the fixed position; and an association mechanism that associates operations of the cassette unit and the cover, wherein a space is created at the fixed position of the cassette unit when the cassette unit is held at the drawn position, and wherein the association mechanism includes a cover restriction portion that restricts the operation of the cover so as to keep the cover at the closed position, at which the cover covers the space, when the cassette unit is held at the drawn position, and a cassette unit restriction portion that restricts the operation of the cassette unit so as to keep the cassette unit at the fixed position when the cover is held at the opened position.

4. The medicine supply apparatus according to claim 3, wherein the cover restriction portion includes a first cover restriction member provided on either the cover or the cassette unit, and a second cover restriction member provided on the other, the first cover restriction member has a hooking portion, the second cover restriction member has a hooked portion to be able to be hooked by the hooking portion, and an open portion where the hooked portion is not provided, the cover restriction portion is configured so that when the cassette unit is at least at the drawn position, the hooking portion is hooked on the hooked portion to restrict movement of the cover to the opened position, and the cover restriction portion is configured so that when the cassette unit is held at the fixed position, the hooking portion passes through the open portion to allow the cover to be moved to the opened position.

5. The medicine supply apparatus according to claim 3, wherein the cassette unit restriction portion includes a first cassette unit restriction member provided on a portion other than the cassette unit, and a second cassette unit restriction member provided on the cassette unit, and the first cassette unit restriction member operates in association with opening and closing of the cover, and engages the second cassette unit restriction member so as to restrict drawing of the cassette unit when the cover is held at the opened position.

* * * * *